US011022607B2

(12) United States Patent
Manivet

(10) Patent No.: US 11,022,607 B2
(45) Date of Patent: Jun. 1, 2021

(54) COMPOUND-CARRIER SYSTEMS FOR ASSAYS IN NEMATODES

(71) Applicant: Assistance Publique—Hôpitaux de Paris, Paris (FR)

(72) Inventor: Philippe Manivet, Paris (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 660 days.

(21) Appl. No.: 14/773,636

(22) PCT Filed: Mar. 7, 2014

(86) PCT No.: PCT/EP2014/054482
§ 371 (c)(1),
(2) Date: Sep. 8, 2015

(87) PCT Pub. No.: WO2014/135691
PCT Pub. Date: Sep. 12, 2014

(65) Prior Publication Data
US 2016/0047796 A1 Feb. 18, 2016

(30) Foreign Application Priority Data
Mar. 8, 2013 (EP) .................................... 13305262

(51) Int. Cl.
*G01N 33/50* (2006.01)
*G01N 33/92* (2006.01)
*A61K 49/00* (2006.01)

(52) U.S. Cl.
CPC ..... *G01N 33/5085* (2013.01); *A61K 49/0008* (2013.01); *A61K 49/0082* (2013.01); *G01N 33/92* (2013.01); *G01N 2333/43534* (2013.01)

(58) Field of Classification Search
CPC ............... G01N 33/5085; G01N 33/92; G01N 2333/43534; A61K 49/008; A61K 49/0082
See application file for complete search history.

(56) References Cited

U.S. PATENT DOCUMENTS

2007/0092558 A1 4/2007 Heavner et al.
2008/0070289 A1 3/2008 Zemach

FOREIGN PATENT DOCUMENTS

EP 2965080 B1 11/2017
JP H03 112924 5/1991

OTHER PUBLICATIONS

Beale, Elmus, et al. "Caenorhabditis elegans senses bacterial autoinducers." Applied and environmental microbiology 72.7 (2006): 5135-5137.*
Bargmann, Cornelia I., and H. Robert Horvitz. "Chemosensory neurons with overlapping functions direct chemotaxis to multiple chemicals in C. elegans." Neuron 7.5 (1991): 729-742.*
English language abstract of JP H03 112924, published May 14, 1991 (from European Patent Office).
Jansen, G., "The G-protein γ subunit gpc-1 of the nematode C. elegans is involved in taste adaptation", The EMBO Journal, vol. 21, No. 5, pp. 986-994, (2002).
Kashima, N. et al., "Development of a method for oral administration of hydrophobic substances to Caenorhabditis elegans: prolongevity effects of oral supplementation with lipid-soluble antioxidants", Biogerontology, vol. 13, pp. 337-344, (2012).
Kojima, M., "High efficiency motility of bacteria-driven liposome with raft domain binding method", Biomed Microdevices, vol. 14, pp. 1027-1032, (2012).
Laing, S. et al., "Characterization of the xenobiotic response of Caenorhabditis elegans to the anthelmintic drug albendazole and the identification of novel drug glucoside metabolites", Biochem. J., vol. 432, pp. 505-514, (2010).
Manjappa, A., "Antibody derivatization and conjugation strategies: Application in preparation of stealth immunoliposome to target chemotherapeutics to tumor", Journal of Controlled Release, vol. 150, pp. 2-22, (2011).
Noppl-Stimson, D.A. and Needham, D., "Avidin-Biotin Interactions at Vesicle Surfaces: Adsorption and Binding, Cross-Bridge Formation, and Lateral Interactions", Biophysical Journal, vol. 70, pp. 1391-1401, (Mar. 1996).
Robert, V. and Bessereau, J.-L., "Targeted Engineering of the Caenorhabditis elegans genome following Mos1-triggered chromosomal breaks", The EMBO Journal, vol. 26, pp. 170-183, (2007).
Schulenberg, H. and Ewbank, J.J., "The genetics of pathogen avoidance in Caenorhabditis elegans", Molecular Microbiology, vol. 66, No. 3, pp. 563-570, (2007).
Shibamura, A. et al., "A method for oral administration of hydrophilic substances to Caenorhabditis elegans: Effect of oral supplementation with antioxidants on the nematode lifespan", Mechanisms of Ageing and Development, vol. 130, No. 9, pp. 652-655, (2009).
Stiernagle, T., "Maintenance of C. elegans", WormBook, ed., The C. elegans Research Community, WormBook, doi/10.1895/wormbook. 1.101.1, http://www.wormbook.org.
Sudama, G. et al., "Metabolic profiling in Caenorhabditis elegans provides an unbiased approach to investigations of dosage dependent lead toxicity", Metabolomics, vol. 9, pp. 189-201, (2013).
Bargmann, C., et al., "Odorant-Selective Genes and Neurons Mediate Olfaction in C. elegans," Cell, vol. 74, pp. 515-527 (Aug. 13, 1993).
Lee, Jungsoo, et al., "Ethanol Preference in C. elegans," Genes Brain Behav., vol. 8, No. 6, pp. 578-585 (Aug. 2009).

(Continued)

*Primary Examiner* — John Pak
*Assistant Examiner* — Daniel L Branson
(74) *Attorney, Agent, or Firm* — Polsinelli PC

(57) ABSTRACT

The present invention relates to methods for increasing absorption of compounds of interest by nematode worms through the design of carrier systems containing said compound of interest and expressing chemoattractive tags at their surface.

15 Claims, 2 Drawing Sheets

(56) References Cited

OTHER PUBLICATIONS

Margie, O., et al., "C. elegans Cemotaxis Assay," Journal of Visualized Experiments, vol. 74, e50069, pp. 1-6 (Apr. 2013).
Shen, P., et al., "Nanoemulsion-Based Delivery Systems for Testing Nutraceutical Efficacy Using Caenorhabditis Elegans: Demonstration of Curcumin Bioaccumulation and Body-Fat Reduction," Food Research International, vol. 120, pp. 157-166 (Jun. 2019).
Yoshida, K., et al., "Odour Concentration-Dependent Olfactory Preference Change in C. elegans," Nature Communications, vol. 3, 739 (Mar. 13, 2012).

\* cited by examiner

Succinimidyl     N-acyl homoserine lactone

COMPOUND-CARRIER SYSTEMS FOR ASSAYS IN NEMATODES

RELATED APPLICATIONS

This application is a national stage application (under 35 U.S.C. § 371) of PCT/EP2014/054482, filed Mar. 7, 2014, which claims benefit of European application EP 13305262.1, filed Mar. 8, 2013.

SUMMARY OF THE INVENTION

The present invention relates to methods for increasing compound absorption by nematode worms, with principal but not exclusive attention devoted to the nematode *C. elegans*. In particular, the present invention concerns the design of polymeric and/or lipidic delivery systems that express specific molecular tags whose characteristics favor the ingestion of the complex "compound-carrier system" by the worm.

BACKGROUND OF THE INVENTION

*Caenorhabditis elegans* (*C. elegans*) is a free-living nematode naturally occurring in soil environments. It rapidly grows from embryo to adult of about 1 mm long and 80 μm in diameter, in approximately 3 days, through 4 larval stages—L1 to L4. Adults are 99.5% hermaphrodite, with occasional male individuals arising from developmental defects. Each self-fertilized hermaphrodite can generate 300 larvae at once. Mature individuals contain a constant number of somatic cells (959 in the adult hermaphrodite and 1031 in the adult male) that recapitulate most major tissue types including epidermis, muscle, neurons, intestine, and sexual reproduction system. Of note, the full sequencing of *C. elegans* genome revealed that 60-80% of the nematode genes have human counterparts and most of the main biochemical pathways are conserved between human and *C. elegans*. Notably, pathways involved in xenobiotic detoxification and oxidative stress response in the nematode are very similar to that of mammalian systems (Voorhies 2002; Lindblom and Dodd 2006). High conservation between the structure and bioenergetics of the worm mitochondria and their human counterparts was also reported (Tsang and Lemire 2003).

*C. elegans* can be easily grown in laboratory conditions, on solid or liquid media containing bacteria, typically *Escherichia coli* (*E. coli*). Its genetic tractability allowed the establishment of a large library of mutant strains (most strains are available at the *Caenorhabditis elegans* Genetic Center, Minnesota). Selective gene knock-down through RNA interference can also be readily performed by injection, feeding or soaking. Furthermore, the worm transparency is a clear advantage for the live worm to be observed, directly or through fluorescent markers.

As a whole, the physical characteristics of *C. elegans* make it an attractive organism for biological research and the nematode has been introduced as a model organism since the 1960s. Notably, it has greatly contributed to our understanding of the mechanisms underlying neuroactivity, ageing, apoptosis, embryonic development and even some human diseases (Brenner 1974; Kuwabara and O'Neil 2001; Gershon and Gershon 2002; Putcha and Johnson 2004; Sengupta and Samuel 2009). By the 1990s, *C. elegans* gained further interest regarding drug discovery and toxicology and emerged as a promising model for mammalian toxicity assessment. When pesticides (Cole, Anderson et al. 2004), metals (Roh, Lee et al. 2006), mitochondrial disruptors (Ishiguro, Yasuda et al. 2001; Braungart, Gerlach et al. 2004) or EGFR kinase inhibitors (Dengg and van Meel 2004) were assessed for their effects on *C. elegans* survival, it was shown that EC50 values in worms strongly correlated with LD50 in rodents.

To study xenobiotic effect on *C. elegans*, compounds to be tested are usually dissolved in the nematode growth medium or poured onto bacteria used for food. However, Burns et al. recently measure the bioaccumulation of commercially available drug-like molecules in the worm and demonstrated that less than 10% of more than 1000 molecules from the Spectrum library readily accumulate (Burns, Wallace et al. 2010). The resistance of the nematode to most xenobiotics can be explained in light of *C. elegans* feeding behavior that tends to limit the ingestion of solutions. As it lives in the soil, the worm developed several protection systems that oppose to the potential entry of harmful substances. The nematode is surrounded by a thick cuticle that blocks extra oral ingress of most molecules. Besides, it functions as a filter-feeder: when food is absorbed, the liquid is spitted out while particles are retained, crushed and enter the intestine (Avery and Shtonda 2003). Hence, a large part of the molecules tested for effects on *C. elegans* may induce no response in the worm, only because they are hardly absorbed and thus fail to accumulate to effective concentrations within the nematode.

To overcome these physiological barriers, the common experimental strategy relies on the incubation of *C. elegans* with high concentrations of substances. Nevertheless this approach has major drawbacks. It requests high quantities of compounds that may not be available, for technical or economical reasons. Furthermore, using such concentrations may induce undesired effects due to the overwhelming of *C. elegans* detoxification effectors or unspecific interactions.

One strategy to promote xenobiotic absorption by the worm without increasing the substance concentration is to enhance nematode permeability, by triggering constitutive pharyngeal pumping for instance. Pharyngeal pumping is the process through which the nematode takes in liquid and then spits it out. It is performed by muscles located in the pharynx whose contraction is controlled by a set of pharyngeal neurons. As pumping mainly occurs in the presence of food, inducing constitutive pharyngeal pumping may favor molecule absorption. It can be achieved by the generation of mutant or transgenic nematodes exhibiting defects in pumping regulation (See patent WO 00/63425 for further information).

However, a strategy based on perturbation of the worm feeding behavior may present significant drawbacks, in the context of drug discovery and toxicology notably. Classically, the assessment of drug efficacy or toxicity in part relies on the analysis of behavioral alterations, including changes in food absorption. Modifying the capacity of the nematode to ingest and accumulate a substance may hence result in the misinterpretation of the mechanism of action of the molecule.

Shibamura et al. developed another approach to favor the absorption of hydrophilic antioxidants. They showed that molecules encapsulated in liposomes increased *C. elegans* lifespan much more efficiently than drugs administered by classical methods (Shibamura, Ikeda et al. 2009).

Accordingly, no method was reported for its use in nematode-based assays, which triggers the absorption of any molecule by the worm, independently from the molecular structure and the physicochemical properties of the substance.

The present invention relates to the design and the use of compound carrier-systems for oral administration to the nematode, which prevent the use of high concentrations and enhance ingestion by the worm.

*Caenorhabditis elegans* is the preferred nematode for this invention, since it is a conventional model organism in biology. Nevertheless, the system hereby described may also be used in the other nematode species, with special emphasis on the *C. elegans* closely related members of the genus *Caenorhabditis*. Wild-type as well as mutant or transgenic nematodes are considered herein.

The *Caenorhabditis elegans* worm was introduced as a promising model organism for biological research years ago and so far, allowed significant advances in the deciphering of mechanisms that underlie a wide array of biological processes including ageing, apoptosis and development. However, the nematode has some limitations that may hinder its use for drug discovery purpose. One main drawback probably concerns its high impermeability to most compounds.

As used herein, the term "assays" refers to any procedure designed to evaluate the impact of any molecule in the worm. For example, it encompasses tests based on the assessment of phenotypic alterations, including, but not limited to, survival, fertility, growth, motility or feeding behavior, as well as the analysis of perturbations at the cellular and molecular levels, including, but not restricted to, changes in enzyme activity, gene or protein expression and regulation, induction of cell death, inflammation and oxidative stress, alteration in respiratory chain function, energetic status and DNA repair systems.

In the context of the invention, the terms "compound" (or compound of interest), "substance" and "xenobiotic" are used indifferently and refer to a foreign molecule that is not normally produced by the worm, but that can be found in its environment or in either natural or experimental conditions. For example, a compound may relate to a chemical substance, such as a small organic molecule, with known pharmacological activity. It can moreover refer to a peptide or nucleic acid molecule, a sugar or saccharide (encompassed are also polysaccharides), a lipid, an organic or inorganic compound, a natural substance, pollutants, solubilized or vapor gas, drugs (including hits and leads from the pharmaceutical industry), substances used in the composition of cosmetic, food, water, beverages, eluents from sewage treatment plants, potential pyrogen substances present in injectable compositions, dialysis waters, substance present in paints and the like.

In order to understand why most compounds are not absorbed by the nematode, its feeding behavior has to be taken into account. *C. elegans* is a soil bacteria-eating worm, endowed with the capacity to discriminate between beneficial and harmful bacteria among a wide array of food sources (Shtonda and Avery 2006; Abada, Sung et al. 2009). It developed a potent chemosensory system that allows it to detect chemicals secreted by bacteria and then preferably directs through the gradient toward high-quality food. These attractant/repellant cues are of diverse origin such as cAMP, biotin, alkaline ions, benzaldehyde, sodium dodecyl sulfate, heptanol (Riddle, Blumenthal et al. 1997). Once the nematode is close enough to its food source, it absorbs it through pharyngeal pumping: pharyngeal muscle contraction directs bacterial particles towards the intestine while liquids are spitted out.

Accordingly, herein is described the production of carrier systems that express specific molecular entities at their surface that possess an attractant effect for *C. elegans*.

The invention thus relates to a carrier system for inducing uptake of a compound of interest by a nematode, comprising a vesicle able to entrap said compound, wherein said vesicle presents, on its surface, a tag substance that is chemoattractive to said nematode. In the preferred embodiment said carrier system consists of said vesicle comprising said chemoattractive tag substance on its surface, and containing said compound of interest entrapped within said vesicle. Consequently, in this embodiment, said carrier system does not consist in an empty vesicle presenting said tag substance on its surface.

In a preferred embodiment, said tag substance is covalently linked to the surface of said vesicle.

JP03112924, US20070092558, Kojima (Biomed Microdevices, 2012, 14:1027-1032) describe liposomes, the surface of which is modified with substances, but don't suggest their use as carrier for having a nematode feed on test substances of interest.

Carrier Systems to be Absorbed by the Nematode

As used hereinafter, the term "tag" (or tag substance) refers to a molecular entity that favors the carrier absorption by the nematode. Preferably, said tag is chemo-attractive to the nematode.

As intended herein, a "chemo-attractive agent" is a chemical agent that induces movement of the nematode in the direction of its highest concentration through chemotaxis. Chemotaxis assays needed to determine the chemo-attractivity of a tag substance for *C. elegans* are known in the art and are described in the art, such as the one described in Jansen et al. (EMBO Journal, Vol. 21 No. 5 pp. 986-994, 2002), which also cites other documents relating to such assays. Consequently, any substance, that has been shown to be, by itself, chemo-attractive to the worm by any chemotaxis assay, can be used as a tag for performing the invention.

Chemotaxis to water-soluble compounds can be assessed by the following method: Briefly, pairs of opposite quadrants of four-quadrant Petri plates are filled with buffered agar either containing a putative dissolved attractant or no attractant. Adjacent quadrants are connected with a thin layer of molten agar. A population of well fed, young adult nematodes is washed buffer and 100-200 worms were placed at the intersection of the four quadrants. The distribution of the worms over the four quadrants is determined after some time. A chemotaxis index [CI=(A−C)/A+C; where A is the number of worms over quadrants 1 and 3, C is the number of worms over quadrants 2 and 4] can be calculated at each time point.

In the context of the invention, the term "entrapped", as in "entrapped compound", is used to designate a compound that is encapsulated, adsorbed or dispersed in a vesicle, or embedded in the layer(s) of a vesicle.

The terms "vesicle" and "carrier" refer to molecular or supramolecular systems endowed with the capacity to store substances. These structures include, but are not limited to, micelles, liposomes, polymersomes, micro and nanoparticles. They also encompass bacterial ghosts and viral vectors which consist in cytoplasm free cell envelopes from Gram-negative bacteria and viruses respectively.

So far, compound carriers have proven instrumental in cosmetics, diagnostics and therapeutics fields, notably imaging and cancer treatment, for oral or dermal delivery of a wide array of molecules, including, but not restricted to, xenobiotics, peptides or proteins, and nucleotidic sequences, in particular DNA and siRNA. They were shown to greatly improve drug bioavalability and reduce adverse effects by allowing controlled release and site-specific delivery in particular (Barratt 2003).

In the context of the invention, the expression "supramolecular system" relates to a complex of molecules joined together through non-covalent or covalent bonds or through both. These molecules include, but are not limited to, lipids, proteins, oligosaccharides and synthetic or natural polymers, and can assemble in various shapes such as spheres, cylinders or rods. Their dimension ranges from nanometers to micrometers.

The term "micelle" designates a colloidal dispersion comprised of an aggregate of amphiphilic molecules that formed a closed monolayer. In an aqueous solvent, the hydrophilic head of the molecules are pointing towards the surrounding solvent while the hydrophobic tails are sequestered in the center of the micelle.

As used hereinafter, the term "liposome" refers to an artificial vesicle of the micrometer-range, whose membrane is composed of a lipid bilayer or series of lipid bilayers surrounding an aqueous core. The bilayers can also contain macromolecules with lipidic moieties such as lipoglycans or lipoproteins, as well as non-lipidic lipophilic or amphiphilic molecules, including, but not limited to, proteins, glycoproteins, polymers or oligosaccharides. Liposomes can encapsulate both hydrophobic and hydrophilic compounds, ionized or not, polar or not, with optical properties like fluorochromes, as well as peptidic sequences and nucleotidic plasmids.

The term "lipid" is understood to include: all classes of naturally occurring lipids i.e. fatty acids, glycerolipids, sterol derivatives, glycerophospholipids and sphingolipids, etc.

A "polymersome", or "polymer-based liposome", designates a synthetic vesicle whose membrane is comprised of amphiphilic block copolymers. The term "copolymer" refers to a polymer derived from several distinct monomeric species whereas "homopolymer" refers to a polymer containing only one monomeric species. A "block copolymer" relates to a copolymer comprised of several different homopolymers. Hydrophilic blocks include, but are not limited to, polyethylene glycol/polyethylene oxide (PEG/PEO) and poly(2-methyloxazoline) while hydrophobic blocks encompass, but are not restricted to, polydimethylsiloxane (PDMS), polycaprolactone (PCL), polylactic acid (PLA) and poly(methyl methacrylate) (PMMA).

In the context of the invention, the term "nanoparticles" relates to vesicles of the nanometer range endowed with the capacity to entrap compounds. The nanoparticles can adopt distinct shapes such as, spheres, rods, tubes or films. Their membranes can be comprised of different types of molecules, including, but not limited to, proteins, in particular gelatin, and/or polysaccharides, such as chitosan or cellulose derivatives, cyclodextrines. Both copolymers and homopolymers, from natural or synthetic origin, can also be components of nanoparticle membrane. We should moreover mention nanosomes that can be defined as nanoscale liposomes. As for liposomes, non-lipidic molecules and substances with lipidic moiety can be embedded into the bilayers of nanosomes in addition to lipids. Nanoparticles can furthermore incorporate inorganic molecules, including, but not limited to, metals, in particular iron, gold, silver or platinum, as well as carbon as in nanodiamonds or carbon nanotubes, ceramics including silica or composite as in calcium phosphate nanocomposites and dendrimers.

Methods Used to Graft the Tag at the Surface of Carriers.

Beyond the advantages the carrier systems described above display for diagnostic and therapeutic applications, it has to be emphasized that they present at their surface, substance that are chemo-attractive to the nematode, thereby sharing some similarities with bacterial particles.

The tag, as the ones described below, shall be grafted on the carrier surface to be accessible to the nematode or the bacteria.

The invention also relates to ways of binding the tag to component of the carrier membrane. According to the definition of the carrier, the vesicle membrane can be comprised of lipids, polymers, proteins and/or saccharides as well as distinct amphiphilic molecules that can bear functional chemical entities able to react with diverse molecules. In the present invention, the tag is bound to one or more components of the carrier membrane, or, according to another approach, linked to a distinct hydrophobic or amphiphilic molecule endowed with the capacity to insert into the carrier membrane. In the context of the invention, the tag can be directly attached to these molecules or can be linked through a spacer, including, but not restricted to, a chemical entity, a peptidic sequence or a monomer/polymer (Accardo, Morisco et al. 2011).

In a preferred embodiment, the tag is linked to a lipid that composes the carrier membrane, in particular, lipid A, the lipidic moiety of LPS, or a phospholipid/phospholipid-derivative, more specifically derivatives of phosphatidylethanolamine and/or phosphatidylcholine. This technique has already been successfully used to attach a wide array of molecules, including, but not limited to, polymers, such as PEG (Allen 1994), or polysaccharides, including oligomaltose (Xu, Jayaseharan et al. 2002), or other chemicals such as biotin (Noppl-Simson and Needham 1996).

In another preferred embodiment, the tag is attached to a polymer, including, but not limited to, the ones previously mentioned, which is directly incorporated into the carrier membrane or bound to a lipid embedded into the carrier membrane. For instance, this strategy was used to graft polysaccharides on polymers derived from poly(vinylamine) (Qiu, Zhang et al. 1998), or attach primary amino group-containing molecules to PEG and PEG derivatives (Torchilin, Levchenko et al. 2001; Santos, da Silva et al. 2010).

In a further particular embodiment, the tag is attached to a molecule encompassing a hydrophobic domain that incorporates into the carrier membrane, including, but not limited to, porphyrins. Porphyrins are heterocyclic macrocycles made of four modified pyrrole subunits linked at their α-carbon atoms through methine-derived bridges. Glyco-conjugated porphyrins were synthesized by linking carbohydrate subunits to a porphyrin core (Ballardini, Colonna et al. 2003; Ballut, Makky et al. 2009) and were then successfully incorporated into the membrane of liposomes composed of dimyristoylphosphatidylcholine (Ballut, Makky et al. 2009; Makky, Michel et al. 2011). Considering the synthesis scheme of these glycodendrimeric porphyrins, other units, distinct from carbohydrates, and including, but not restricted to, peptidic fragments, chemicals, can be attached to porphyrin cores.

Design of Tags and Carrier Systems for the Chemo-Attraction of the Nematode (FIG. 1)

As for most carriers mentioned herein, bacteria size ranges between 0.5-5 µm in diameter for spherical species and 0.2-2 µm in diameter and 1-10 µm in length for rod-shaped bacteria. The smallest species range between 100-500 nm while the largest ones can reach 500 µm in diameter. Furthermore, bacteria are surrounded by a cell membrane that is almost exclusively comprised of a phospholipid bilayer in which various other molecules are embedded, including, proteins and polysaccharides.

Hence, one strategy to trigger compound absorption by the nematode would be to entrap this molecule within a bacterium-like particle so as to fool the worm and have it believe it ingests a true bacterium. This hypothesis was tested by Shibamura et al. They encapsulated antioxidant molecules into liposomes made of L-α-phosphatidylcholine and showed enhanced effect of entrapped molecules compared to classically delivered substances on *C. elegans* lifespan (Shibamura, Ikeda et al. 2009). However, one has to keep in mind that the nematode is able to discriminate between high-quality food and poor-quality one. With experience, it acquires the capacity of only eating the better bacteria while keeping away from the less nutritive ones. So, it is postulated that, throughout the experiment, the nematode may eventually stop ingest the liposomes as they are mentioned above.

In order to have the nematode keep eating the compound-containing vesicles, the solution is to use a carrier system mimicking the bacteria the nematode usually eats thereby having the compound ingested by the worm. Said carrier system includes, but is not restricted to, the vesicles as described above and comprises a tag on its surface.

In experimental conditions, the favorite bacteria used as food source are *Escherichia coli*, notably the uracil-auxotroph OP50 strain. The carrier in which the compound is entrapped is added to the cultivation medium of the nematode, alone or in addition to the bacterial source of food.

One important parameter for the choice and design of the carrier may be its size since, during pharyngeal pumping, too small vesicles could be spitted out concomitantly with liquid instead of being addressed to the intestine (Fang-Yen, Avery et al. 2009).

In a preferred embodiment, the carrier system is of a size which compares to the size of bacteria, in particular the size of Gram-negative bacteria, more specifically, the size of *Escherichia coli*. In a preferred embodiment, the carrier system's size ranges from 0.5 to 3 µm. It is preferably a liposome.

In a particular embodiment, the carrier system is a liposome mainly composed of glycerophospholipids. Said lipids may be phosphadityletanolamine, phosphatidylglycerol and cardiolipin alone or as mixtures. Other lipids may also be used, either as main component of the liposome, or as minor component of the liposome.

The liposome may also comprise lipopolysaccharide (LPS), which are essential components of the outer membrane of Gram-negative bacteria, including *Escherichia coli*.

The present invention also relates to the design of a tag-molecule present (either incorporated, grafted (linked to the surface via a linker) or covalently linked) at the surface of the compound-carriers so as to trigger their efficient absorption by the nematode whatever the cultivation conditions are, in particular whatever the food source is.

*C. elegans* possesses a potent chemosensory system that enables it to respond to a wide array of chemicals, in particular to exoproducts released by bacteria possessing a quorum sensing (QS) machinery (Beale, Li et al. 2006). QS is a strategy developed by both Gram-positive and Gram-negative bacteria for cell-to-cell communication, involving the secretion and detection of hormone-like signaling molecules termed autoinducers (Antunes and Ferreira 2009). QS leads to coordinated behavior and mediates a wide array of processes such as virulence, antibiotic production, motility or conjugation. The autoinducers include, but are not restricted to, the autoinducer AI-2 produced by nearly all species, acylated homoserine lactones (AHSLs) secreted by most Gram-negative bacteria and oligopeptides for some Gram-positive species. Regarding *E. coli*, the main autoinducer is AI-2. *E. coli* bacteria do not produce AHSLs contrary to other Gram-negative bacteria, but nevertheless possess receptors for AHSLs.

AI-2 is a furanosyl borate diester that is exported from *E. coli* through the transporter TqsA and is then internalized by an Lsr import protein (De Araujo, Balestrino et al. 2010).

AHSLs encompass a large variety of molecules composed of a fatty acyl chain ligated to a lactonized homoserine through an amide bound. The acyl chain can be either saturated or not and vary in length between 4 and 16 carbons. The third carbon in the acyl chain can moreover undergo various modifications, including being fully reduced, being a fully oxidized carbonyl or carrying a hydroxyl group (Fuqua and Greenberg 2002).

The peptides mediating Gram-positive bacteria QS are native and post-translationally modified linear and cyclic peptides that vary in the number of their amino acids, classically ranging from 5 to 60 amino acids (Fuqua and Greenberg 2002).

In a preferred embodiment, the tag comprises part or all of an autoinducer produced by a Gram-negative bacterium, as described above.

In particular, the carrier is modified as to have, incorporated at its surface, a molecule encompassing one or several moieties corresponding to an AHSL- or AI-2 molecule or fragment.

In another embodiment, the tag inserted in the carrier membrane comprises to a molecule, including, but not restricted to, peptide and polysaccharide, endowed with the ability to interact with a bacterial autoinducer, thus favoring the accumulation of the QS signaling molecules around the vesicle. In particular, said autoinducers is AHSLs or AI-2.

In this embodiment, said molecule which interacts with said autoinducer comprises a full protein, or a fragment of a protein matching or with similar properties to the binding domain of one bacterial receptor for AHLS or AI-2. The tag molecule may thus comprise of be a stretch of few amino acids able to interact with and/or be recognized by these autoinducers. Such peptides may be designed through molecular modeling and validated with binding assays of recombinant molecules.

In another embodiment, the ligand for autoinducers comprises be LPS as some QS molecules can interact with LPS at the outer membrane of Gram-negative bacteria (Mashburn-Warren, Howe et al. 2008).

The tag may also be another chemoattractive molecule, distinct from a bacterial autoinducer. It may be a water-soluble molecule, including, but not limited to, salts, some amino acids, such as cysteine, lysine and histidine, some nucleotides like cAMP and cGMP and some vitamins as biotin, or volatile molecules, including, but not restricted to, various alcohols, ketones, aldehydes, esters, ethers, thiazoles, pyrazines and aromatics (Riddle, Blumenthal et al. 1997).

It is thus foreseen to design a tag that derived from the chemoattractants as described above or that is endowed with the capacity to bind these molecules, such as to be coated with these molecules when presented to the nematode.

In a preferred embodiment, biotin is used as a chemoattractant for the nematode.

In particular, biotin can be directly grafted at the surface of the carrier. In order to enhance the biotin concentration around the carrier, biotin and a biotin-binding molecule, more specifically a biotin-binding protein, in particular avidin or streptavidin, is added to the cultivation medium in which the carriers are poured (Noppl-Simson and Needham 1996). The biotin-binding molecule displays at least two biotin-binding sites, preferably at least 3 biotin-binding sites, so as to aggregate biotin in the immediate vicinity of the vesicle. Avidin and streptavidin are two tetrameric proteins that can bind up to four molecules of biotin simultaneously with a high degree of affinity and specificity. In another embodiment, a biotin-binding molecule, including, but not limited to, the ones mentioned above, is incorporated at the carrier surface, so the biotin present in the cultivation medium can accumulate around the vesicle. In another embodiment, said tag substance is avidin.

Design of Linkers and Carrier Systems for the Capture of Bacteria (FIG. 1)

As previously mentioned, because carriers are less nutritive than bacteria, the nematode could neglect them and prefer better-quality bacteria upon experience.

According to another strategy, one can design a linker that can bind to bacteria, in particular Gram-negative bacteria, more particularly *Escherichia coli*, so as to have the carrier ingested concomitantly with bacteria. In this context, one would consider that the chemoattractive tag linked to the carrier system is actually the whole bacterium. Effectiveness of this strategy has been confirmed by Däwlätsxina et al (2013).

In these particular embodiments, the size of the carrier system is preferably adapted so that the size of the carrier system attached to the bacteria is small enough to be ingested by the worm. In these particular embodiments, preferred carrier systems will be of the nanometer range, more specifically, nanoparticles or nanosomes.

The cell membranes of Gram-positive bacteria as well as the outer membranes of Gram-negative bacteria are comprised of polysaccharides, such as LPS, and several proteins including structural proteins, enzymes and transporters, in addition to lipids. Not only do these proteins admit a wide array of ligands but also the lipids and polysaccharides that can bind various molecules. For instance, the LPS that is exposed at the outer membrane of Gram-negative bacteria, including *E. coli*, can interact with autoinducers from the AHSL family (Mashburn-Warren, Howe et al. 2008).

Consequently, is also described the expression at the carrier surface of a linker encompassing a molecule including, but not restricted to, chemical, protein, saccharide or lipid, able to interact with a bacterial membrane component including, but not limited to, a lipid, a protein and a polysaccharide.

In a particular embodiment, said linker is a molecule derived from AHSLs. Said molecule may be a degradation product of the tag or linker so that there might be an heterogeneity of the tags at the surface of the vesicle (such as tags that are native or oxidized, reduced or partially degraded, preferably with no loss of the chemo-attractive property).

In another approach, one can focus on the bacterial transporters that mediate uptake of nutrients, more particularly on the maltose/maltodextrin transport system and design a tag encompassing one or more molecular units corresponding to native or modified nutrients that are transported into the bacteria, more specifically Gram-negative bacteria, including *E. coli*. Maltose is a disaccharide formed from two units of glucose joined with an α(1→4) bound. Maltodextrins are linear α(1→4)-linked glucose polymers with variable numbers of units, classically ranging from 3 to 19 glucose units, including starch and amylose, as well as α-(1→4)-glucosidally linked cyclodextrins. The maltoporin LamB, which is also the bacteriophage λ receptor, facilitates the diffusion of maltose and maltodextrins through the outer membrane of Gram-negative bacteria, including *E. coli*. Maltodextrins then interact with the maltose-binding protein (MBP) in the periplasmic space to be transported through the inner membrane towards the cytoplasm (Boos and Shuman 1998; Klebba 2002). LamB mediates the transport of native maltose and maltodextrins but also of modified maltodextrins with reduced, oxidized or substituted glucose units (Ferenci, Muir et al. 1986).

In a particular embodiment, the linker encompasses one or more cyclic or linear polysaccharides derived from maltose.

In particular, said maltose-based polysaccharides are polymers of covalently linked repeated units of maltose chosen in the group consisting of linear polymers, cyclic polymers, brached polymers and mixtures thereof.

More particularly, maltodextrins and analogues with a molecular weight up to 2000 g/mol are preferred since it has been shown that the LPS present on the outer membrane of Gram-negative bacteria interferes with the binding of larger maltodextrins to LamB (Ferenci and Lee 1986). The term "maltodextrin analogues" refers to modified maltodextrins with one or several glucose subunits being reduced, oxidized or substituted, including, but not limited to, O-methyl, 0-nitrophenyl, beta-glucosyl or beta-fructosyl substitutions at the reducing ends of glucose.

In particular, said said linker is a maltodextrin or an maltodextrin analogue with a molecular weight up to 2000 g/mol.

The invention also encompasses any carrier system (as disclosed above) which presents, at its surface, a linker that is able to interact with the surface, and in particular a bacterial membrane component, of a bacterium (preferably a Gram-negative bacterium). Said linker is preferably able to interact with the LPS of said bacterium.

Nutrient Compositions

The invention also relates to a nutrient composition for a nematode, comprising a carrier system as described above, as well as nutrients suitable for the worm. Such nutrients are known in the art and are described in particular in Stiernagle (2006). In particular, the nutrient composition contains sterols. In a specific embodiment, said nutrient composition is such that it contains a carrier system in which said tag substance is biotin and it further comprises biotin and a biotin-binding protein which comprises at least two biotin-binding sites. As indicated above, said biotin-binding molecule displays at least two biotin-binding sites, preferably at least 3 biotin-binding sites, so as to aggregate biotin in the immediate vicinity of the vesicle. Avidin and streptavidin are such proteins that can be present in the cultivation medium as they can bind up to four molecules of biotin simultaneously with a high degree of affinity and specificity.

Use of the Carrier Systems

The carrier systems of the invention are particularly useful for promoting uptake of the entrapped compound of interest by a nematode. This makes it possible to design multiple assays for determining the metabolism of said compound of interest within the worm.

In particular, it is possible to assess the physiological properties of said compound of interest wherein said compound of interest has been trapped in a vesicle presenting a chemo-attractive tag on its surface such as to obtain the carrier system of the invention, by feeding a nematode with a nutrient composition comprising said carrier and assessing said physiological properties of said compound of interest in the nematode after uptake.

The physiological properties of said compound that can be assessed by the methods according to the invention comprise in particular toxicity of said compound, or ADME parameters (Absorption of the compound within the digestive tractus of the nematode, Distribution of the compound within the worm, Metabolism of said compound and Elimination pharmacokinetic). These may be measured by assays that are known in the art. Indeed, the focus of the present invention is not to design assays for assessing the properties of a compound, but rather to design carrier that allow uptake and ingestion of said compound by the worm.

*C. elegans* has already been used for assessing toxicity of compounds (see in particular Sudama et al, Metabolomics. 2013 February; 9(1):189-201). Such assessed toxicity may be acute or chronic toxicity (such assays are described in Wu et al, Chemosphere. 2012 June; 87(11):1281-7).

As for ADME parameters, one can note the work of Laing et al (Biochem J. 2010 Dec. 15; 432(3):505-14), who characterized the xenobiotic response of *Caenorhabditis elegans* to the anthelmintic drug albendazole.

Such assays may be based on analysis of the gene response of *C. elegans* to the xenobiotic compound entrapped within the carrier system.

One can also quantify the absorbed compound of interest when said carrier system further comprises a fluorescent marker encapsulated in said vesicle. This quantity is evaluated by measuring the fluorescence intensity of the co-absorbed fluorescent marker.

The invention also relates to a method for evaluating/determining the impact of a mutation/polymorphism in a gene.

Said method comprises the steps of feeding a nematode in which said mutation/polymorphism is present with a carrier system according to the invention containing a compound of interest, and of comparing the uptake and degradation of said compound of interest with the uptake and degradation of said compound of interest being fed to a nematode in which said mutation/polymorphism is not present.

In view of the above, it is preferred when said gene codes for a protein that is the target of said compound of interest (which can be a medicament), or when said gene is an effector of a xenobiotic transformation (or metabolism), such as a cytochrome.

In performing said method, one would identify the nematode ortholog of the human gene for which one wish to study the effect of the polymorphism/mutation. In particular, it is possible to use databases such as the Wormbase (www.wormbase.org) and the Blast program (preferably the blastp program to identify the nematode ortholog of a human ortholog. This is well known in the art.

Said mutation/polymorphism can be introduced in the nematode ortholog gene by method known in the art for manipulating the *C. elegans* genome, such as the ones described by Barrett et al (Nat Genet. 2004 November; 36(11):1231-7), Robert and bessereau (EMBO J. 2007 Jan. 10; 26(1):170-83), Frøkjaer-Jensen et al (Nat Genet. 2008 November; 40(11):1375-83) or Bazopoulou and Tavernarakis (Genetica. 2009 September; 137(1):39-46).

Using the above-mentioned method, it is possible to identify polymorphisms that are able to potentiate the metabolism assimilation of some medicaments, or conversely to identify polymorphisms which, when present, don't allow the medicament to exercise its biological activity.

Methods Used to Quantify the Concentration of the Encapsulated Xenobiotics Absorbed by the Worm.

One major issue for xenobiotic toxicity evaluation and measure in alternative in vivo models like *C. elegans* is the quantification of the amount of the compound absorbed by the worm that is directly correlated to its toxicity. Not all the encapsulated quantity of the compound reaches the nematode organs. Indeed, some amount of the compound will be lost along the diffusion of the carrier in the *C. elegans* culture medium, degraded and/or eliminated in the worm digestive tract, etc.

In the assays hereby described, molecules with optical properties such as fluorescent markers may be co-encapsulated inside the carrier with the xenobiotic/compound of interest. Since the worm is transparent, it is possible to measure the quantity of the absorbed xenobiotic by measuring the fluorescence intensity of the co-absorbed fluorescent marker. The fluorescent markers shall preferably be selected for their absence of toxicity for the worm.

In another embodiment, one can use this technique to standardize different assays by normalizing the absorbed concentration of the carrier and then the xenobiotic with the fluorescence intensity of the fluorescent marker. The toxicity measure can be then reported to the quantity of the absorbed xenobiotic.

EXAMPLES

Materials

Hydrogenated soybean phosphatidylcholine (HSPC), 1,2-distearoyl-sn-glycero-3-phospho ethanolamine-N-[PEG (2000)] conjugate (DSPE-PEG), and DSPE-PEG(2000) Amine (DSPE-PEG-NH2) were obtained from Northern Lipids Inc (Vancouver, BC, Canada). Cholesterol was obtained from Sigma, (St Louis, Mo.).

Drug to be loaded inside liposomes can be selected within the list of 1000 compounds with tested bioaccumulation inside *C. elegans* previously published by Burns et al in 2010. Other compounds of interest, as described above, can also be used.

In order to evaluate the efficiency of the present invention, two sets of compounds may be tested:
  those known as easily accumulated in *C. elegans* to concentrations greater than 50% of that present in the worm's environment, and
  those that cannot evade the worm's defenses and never penetrate in the animal.

Figure 1:
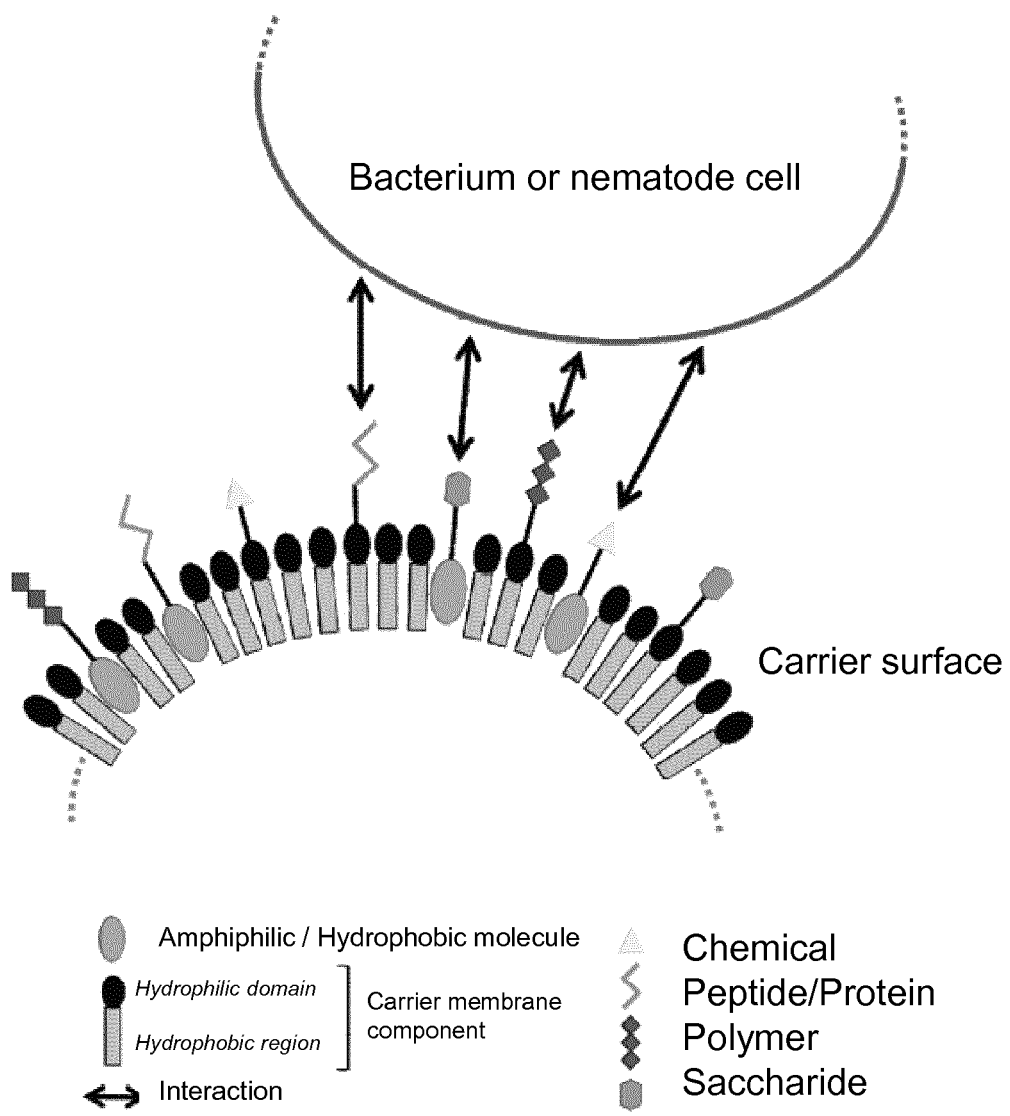
FIG. 1: Schematic representation of the different tags designed to be grafted at the carrier surface.
Figure 2:
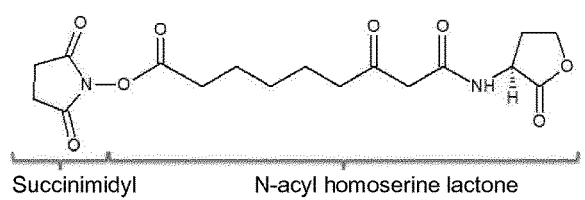
FIG. 2. Succinimidyl N-(8-Carboxy-3-oxooctanoyl)-L-homoserine Lactone that is one of the most worm attractive serine lactones [5].

Selection of attracting substances sniffed by the worm in the medium (N-acylhomoserine lactone (AHL)) was done based on the work of Beale et al published in 2006 [5] (FIG. 2). These were synthesized as previously described [Chhabra, 1993; Chhabra, 2003]. They were then grafted on DSPE-PEG-NH2.

1. Preparation of Liposomes

Liposomes were composed of HSPC, cholesterol, and DSPE-PEG-NH2 in the molar ratio of 65:30:5, respectively.

Accurately weighed amounts of lipids (325 µmol HSPC, 150 µmol cholesterol, and 25 µmol DSPE-PEG) and drug (100 µmol) were dissolved in chloroform:methanol (9:1 vol/vol) in a round-bottom flask.

After mixing, solvent was evaporated under reduced pressure and constant rotation (Rotovapor R-200, Buchi, Flawil, Switzerland) to form a thin lipid film. The lipid film was then hydrated with 50 mM HEPES/150 mM NaCl-buffer pH 6.5 (5 mL) at 62° C. for 2 hours to form large multilamellar vesicles (MLV) at 100 mM total lipid concentration.

The resulting MLV were then sized by repeated extrusion (Lipex extruder, Northern Lipids) through polycarbonate membranes (Nucleopore, Whatman, N.J.) of gradually decreasing pore size (0.8, 0.4, 0.2, and 0.1 µm) to prepare small unilamellar liposomes of ~100 nm in diameter [Hope, 1985].

Extrusions were performed in a 10-mL size thermobarrel extruder at 62° C. After extrusion, liposomes were stored at 4° C. until used in subsequent experiments.

Liposomes were loaded with fluorescent dye in order to control the success of oral delivery of chemical chemicals into the intestines of *C. elegans*. Based on the experiments of Shibamura A et al [2009], 25 ml of liposomes containing 50 mg of uranin allow an amount of fluorescent dye absorption in 3 h 100-fold higher as compared with worms administered dye by conventional methods. In addition, fluorescent dye liposome incorporation allows calibrating the amount of drug accumulated by worms.

2. Preparation of Tagged Liposomes

Figure 3:
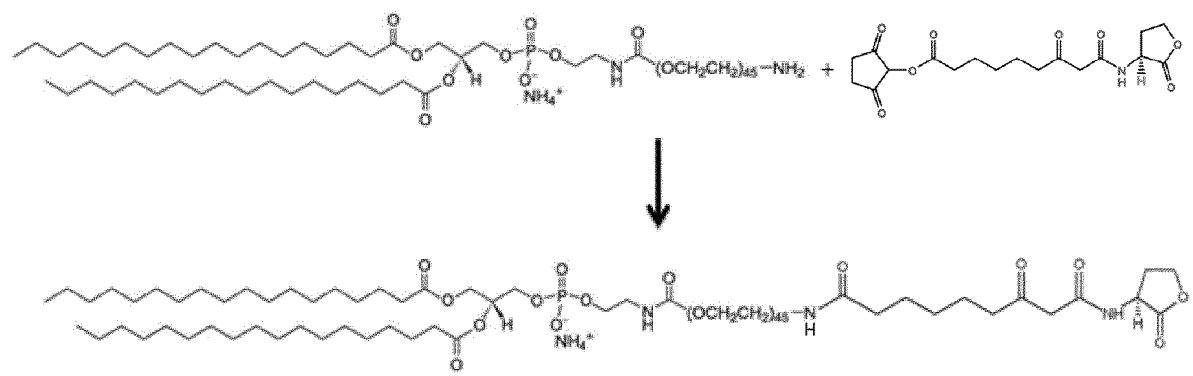
FIG. 3. N-(8-Carboxy-3-oxooctanoyl)-L-homoserine Lactone grafted on DSPE-PEG-NH2 (chlorhydrate form=—NH3+, Cl—).

For preparation of tagged liposomes, AHL derivatives were coupled to the distal end of PEG chains on the liposomes. To enable this ligand coupling, a part of (2 mol %) DSPE-PEG in the liposome formulation was replaced with DSPE-PEG-NH$_2$ functional lipid. Total lipid concentration of the liposomal dispersion used for the coupling reaction was 100 mM. AHL was dissolved in 50 mM HEPES buffer, pH 6.5 at 2.7 µmol/mL concentration (0.1 mL), were reacted with liposome (4 mL) with NH$_2$ functional groups on the distal end of PEG chains at pH 6.5 and a molar ratio of 1:30 (AHL) for 12 hours at room temperature (25° C.). A schematic representation of the coupling reaction is given in FIG. 3.

3. HPLC Determination of AHL Coupling to the Liposomes

Attachment of AHL to the liposome surface was ascertained indirectly by determining non coupled AHL fraction using HPLC.

Analytical reverse-phase high-performance liquid chromatography (RP-HPLC) was performed using an analytical column (HiChrom Kromasil KR100-5 C 8; 250 mm×4.6 mm) with a Waters 625 LC system attached to a Waters 996 photodiode array system operating with a Millenium 2010 Chromatograph Manager. Fractions were eluted with a linear gradient of acetonitrile in water (70-100%, v/v) over a 20 min period at a flow rate of 0.7 mL min-1 and monitored at 210 nm. Semi-preparative HPLC was performed with a C8 reverse-phase preparative column (HiChrom Kromasil KR100-5 C 8; 250 mm×8.0 mm) using a Gilson system. Fractions were eluted with an isocratic system, and determined from the analytical HPLC data, at a flow rate of 2.0 mL min-1.

4. Estimation of Drug Entrapment in Liposome Formulation

Total and free drug "x" in the liposome formulations were determined using HPLC analysis.

In a specific embodiment, drug "x" can be combretastatin A4. Combretastatin is well known for producing quinine derivatives under oxidative metabolism. Quinones bind nucleophiles and enhance oxidative stress by generating radical species [Folkes et al, 2007].

The toxicity of this molecule is measured and characterized with a series of "stress" and "anti-stress" enzymatic activity assays detailed below in paragraph 8.

Total drug was determined after ethanol extraction. An aliquot of the liposome dispersion (50 µL) was diluted to 2 mL with ethanol to release liposome-encapsulated combretastatin A4. Total combretastatin A4 in this clear ethanol extract was determined using HPLC, with a C 18-column (Nova-Pak 3.9×150 mm column, Waters) and methanol:water (50:50) as mobile phase. Flow rate of 0.8 mL/min and UV detection at 295 nm were used. Free combretastatin A4 was separated from the liposome encapsulated part using a Centricon centrifugal filter device (Centricon 10, MWCO 10 kd, Millipore, Bedford, Mass.). An aliquot of the liposome dispersion (100 µL) was diluted to 1 mL with hydration buffer (50 mM HEPES/150 mM NaCl-buffer pH 6.5), and this sample was transferred to the centrifugal filter device. The sample was centrifuged at 10 000 rpm for 15 minutes in a fixed-angle centrifuge. Free combretastatin A4 in the filtrate was then determined using HPLC. Dilution factors were taken into consideration for calculation of total and free drug. Subtraction of free drug from the total drug gave the amount of liposome-entrapped drug. Drug estimations were done in triplicate, and the values were reported as mean±SEM. One can adapt this method with another drug.

5. Visualization and Size Measurements

Large MLV, before the extrusion process, were visualized using a light microscope (Olympus, CKX41, Tokyo, Japan). Final liposomes were visualized under electron microscope by negative staining technique. A diluted liposome sample was adsorbed onto a formavar- and carbon-coated copper grid, stained with 2% uranyl acetate (pH 7.0) and observed with a JEM1200EX electron microscope (JEOL, Tokyo, Japan) at ×50 000 magnification. Size and size distribution profiles of liposomes were monitored by dynamic light scattering method using the Malvern Zetasizer (Nano ZS, Malvern Instruments, Worcestershire, UK).

6. In Vitro Leakage Studies

Liposome encapsulation stability of combretastatin A4 was monitored in vitro, by dialyzing samples for 48 hours against 700 volumes of reverse osmosis water maintained at 37° C.

A 0.5-mL aliquot of the liposome dispersion was placed in a presoaked Pierce dialysis cassette (Slide-A-Lyzer, MWCO 10 kd, Millipore), which was then placed in a beaker containing 350 mL of release medium pre-equilibrated to 37° C. The dialysis cassette was rotated at 100 rpm. The volume of release medium was selected based on careful consideration of sink conditions and sensitivity of the analytical method. At different time points, 0.5-mL samples were taken from the release medium and replaced with an equal volume of fresh release medium. Samples were analyzed for the released drug, combretastatin A4, using the HPLC method of analysis.

From the total drug concentration of the liposome formulation, percentage released at each time point was calculated. Results are reported as mean±SEM (n=3).

7. High-Throughput Screening of Small Molecules in *Caenorhabditis elegans*

Culture worms were performed according to established protocols [Lewis and Fleming, 1995; Stiernagle, 1999]. HTS experiments were performed according to Burns et al [2010 and 2006]. Late-stage fourth-larval-stage worms, grown from synchronized hatchlings at 25° C. for 45 h on NA22 *Escherichia coli*, were used for the accumulation assay. The worms were harvested, washed at least twice and resuspended in enough M9 buffer1 for a final concentration of ~10 worms per µl. Five hundred microliters of this worm suspension was added to each well of Pall AcropPrep 96-well filter plates (0.45-µm GHP membrane, 1-ml well volume).

Liposomes were added to each well in order to obtain a final concentration of chemicals of 40 µM (0.4% DMSO, v/v). Worms were incubated in the small-molecule solutions at 20° C. for 6 h with aeration, after which the incubation buffer was drained from the wells by vacuum (the filter membranes weaken if incubation is longer than 6 h).

The worms were then washed three times with 500 µl of M9 buffer. After washing, the worms were resuspended in 50 µl of M9 buffer, transferred to new 96-well solid-bottom plates and stored frozen at −20° C. The samples were later lysed by adding 50 µl of a 2× lysis solution (100 mM KCl, 20 mM Tris, pH 8.3, 0.4% SDS, 120 µg ml$^{-1}$ proteinase K) to each well and incubating the plates at 60° C. for 1 h with agitation. After lysis, the plates were stored frozen at −80° C. for later processing by HPLC (see Supplementary Methods for the full HPLC methods in Burns et al [2010]).

8. Post Processing HTS of Small Molecules in *Caenorhabditis elegans*[2]

*Caenorhabditis elegans* is a versatile in vivo platform for a wide range of applications [Jones et al, 2005; Artal-Sanz, 2006] like screens for human drugs, drug target identification and validation, or mode of action of drugs, screens for ADME (Adsorption, Distribution, Metabolism, and Elimination/Excretion) and Toxicity parameters of pharma hits and leads and xenobiotics for eco- and environment toxicity, cosmetology, study of major cell signaling pathways like apoptosis, inflammation, oxidative stress, respiration, cell energetic, control of water (henodialysis, drinking water, for parenteral injection) contamination by chemicals and bacteria toxins, etc.

Among all these applications, ADME-Tox parameters in the most challenging task since pharmaceutical industry is still confronted to harmful lead drug toxicity lately revealed during the clinical phases.

*C. elegans* can be very efficient tool for achieving this screening if only coupled with the present invention.

The different field of applications mentioned above need a large panel of experimental techniques for analysis of *C. elegans* treated with drugs.

Among the available technique the most popular are biochemistry assays (enzymology, proteomics, metabolomics, transcriptomics, miRNA, etc), cell imaging, mutagenesis, gene knock out, etc.

8.1. Toxicity Screening

Table 1 summarizes toxicity endpoints that can be measured in worms. These endpoints concern either pharmaceutical industry or cosmetology for instance for their lead therapeutic and cosmetic compounds respectively.

Toxicity screening can be easily achieved on frozen worms stored at −80° C. as described in paragraph 7. For instance respiratory chain complexes activities can be automatically measured on hospital biochemistry lab apparatus based on the protocol previously described by Kramer et al in [2005].

In addition, anti-stress enzymes and metabolites can also be measured on the same sample, like SOD [McCord and Fridovich, 1969], GPX [Paglia and Valentine, 1967], GRed, oxidized and reduced glutathione [Beutler and Mitchell, 1968], G6PDH [Krien et al, 1992].

Excess of reactive radical oxygen species, alteration of one or several main cell metabolic pathways, modification of the imbalance between stress and anti stress enzyme activities, can be rapidly and accurately measured on few hundreds worms.

| ENDPOINT | ASSAY |
|---|---|
| Survival | Dose-response |
| | Kinetics of survival |
| | Acute/Chronic/Repeated doses toxicity |
| Cytotoxicity | Large panel of biomarkers: stress ox; respiratory chain; apoptosis; cell energetic; inflammation; cytochromes function; main cell metabolic pathways like Krebs, glycolysis, β-oxidation, glycogenolysis, glycogenogenesis, miRNA expression, etc |
| | In situ fluorescence |
| | Acute/Chronic/Repeated doses toxicity |
| Toxicokinetics | Assessment of the accumulation of the molecule and its metabolites |
| | Changes in the expression of CYPs/GSTs/Transporters |
| | Impact of the knock-down of a CYP/GST/transporter |
| Reprotoxicity | Assessment of the egg-laying behavior |
| | Measurement of the gonad functionality |
| Teratogenicity | Embryonic lethality |
| | Time of development |
| | Analysis of molecular markers specific for each larval stage |
| Neurotoxicity | Neuronal death |
| | Quantification of neurotransmitters and their metabolites |

8.2. Analysis of Chemicals Metabolites by LC-MS

Metabolites were HPLC-purified from worm lysates and dried using a Savant DNA120 SpeedVac (acid was not added to the HPLC solvents).

Chromatographic separations of the purified metabolites for LC-MS were performed using a nano-AQUITY Ultra Performance Liquid Chromatography (UPLC) system (Waters Corp.) (see Supplementary Methods for full methods in Burns et al (2010)).

Mass spectrometry was performed using a Micromass Quadrupole-Time-of-Flight Premiere instrument (Waters Corp.). The data acquisition software used was MassLynx NT, version 4.0. Mass spectra were acquired in positive ion mode using a nano-ESI with capillary voltage and sample cone voltage set to 3,000 V and 20 V, respectively. The MS acquisition rate was set to 1.0 s, with a 0.1-s interscan delay. Ninety-eight percent argon gas was employed as the collision gas with collision energy varying from 13-46 V for the mass range of 100-1,000 m/z. Ions selected for LC-MS-MS were identified after manual analysis of original LC-MS runs, and a corresponding inclusion list was generated for targeted data-dependent acquisition experiments.

8.3. Different Strain of *C. elegans* for ADME Tox Screening

Several wild type (WT) strains of *Caenorhabditis elegans* are available (see in particular https://www.cbs.umn.edu/cgc/strains (College of Biological Sciences, University of Minnesota), the most common being the strain N2).

By measuring the same biochemical alterations induced by accumulation of a specific chemical in different WT strains, it is possible to validate accurate biomarkers that are associated with a specific toxicity mechanism.

By following the evolution of the toxicity along the time, it is possible to predict impact of such alterations on the worm lifespan.

A large number of mutant strains of *C. elegans* also exist and are available at the *Caenorhabditis* Genetics Center of Minneapolis, USA, for instance.

Knock-out strains for one or several molecular actors of the cell metabolic pathways are very useful for anticipating the drug toxicity in mammalians.

Indeed, detoxification mechanisms are very similar in mammalians and *C. elegans* [Lindblom and Dodd, 2006].

The structure and the function of the mitochondria of *C. elegans*, particularly in relation to oxidative stress, are very close to those observed in humans [Murfitt et al, 1976].

The main enzymes involved in the metabolism of xenobiotics are found: cytochrome P450 (78 genes), short-chain dehydrogenases—SDR (68 genes), or UDP-glucuronosyl-transferases glycosyl—UGT (63 genes), flavin-monooxydases—FMO (5 genes), glutathione S transferase—GST (48 genes), sulfotranferases, methyltransferases, acetyltransferases, etc.

It is interesting to note also the presence of carriers ATP-binding cassette (60 genes) involved in the transport of xenobiotics.

In addition, the intestinal cells and those forming the excretory system of the nematode assume the equivalent functions of liver and kidney found in humans.

Several comparative studies have established a classification of substances tested for their potential toxicity in the nematode, showing a correlation with measurements made in rodents [Cole et al, 2004; Dengg and van Meel, 2004; Williams et al, 2000]. These studies validate *C. elegans* as a model organism for assessing the toxicity of a drug.

By comparing the alterations induced by the same chemical in the WT and mutated strains, it is possible to identify and quantify, among the altered cell metabolic pathways, the functional interactions between several molecular actors.

The use of the thermosensitive mutant strain TJ1060, infertile in normal growth conditions at 20-25° C., allows to overcome problems inherent to the rapid fertility cycle of the worm and limit the number of individuals in the plate well. This is a major advantage for the study of chronic toxicity at repeated doses.

A strain like CL2166 expresses some gene coupled to GFP under the control of the glutathion transferase GST-4 promoter. This enzyme is expressed after a xenobiotic stimulus and participates to their metabolization.

In the strain TJ375 GFP expression is controlled by the HSP 16-2 promoter. HSP are sensitive to sepsis, chemical and toxic stress and can be considered as cell stress markers.

REFERENCES

Abada, E. A., H. Sung, et al. (2009). "*C. elegans* behavior of preference choice on bacterial food." Mol Cells 28(3): 209-213.

Accardo, A., A. Morisco, et al. (2011). "Naposomes: a new class of peptide-derivatized, target-selective multimodal nanoparticles for imaging and therapeutic applications." Therapeutic Delivery 2(2): 235-257.

Allen, T. M. (1994). "Long-circulating (sterically stabilized) liposomes for targeted drug delivery." Trends Pharmacol Sci 15(7): 215-220.

Artal-Sanz M, de Jong L, Tavernarakis N. *Caenorhabditis elegans*: A versatile platform for drug discovery. Biotechnol J. 2006, (12):1405-18.

Antunes, L. C. and R. B. Ferreira (2009). "Intercellular communication in bacteria." Crit Rev Microbiol 35(2): 69-80.

Avery, L. and B. B. Shtonda (2003). "Food transport in the *C. elegans* pharynx." J Exp Biol 206(Pt 14): 2441-2457.

Ballardini, R., B. Colonna, et al. (2003). "Porphyrin-Containing Glycodendrimers." European Journal of Organic Chemistry 2003(2): 288-294.

Ballut, S., A. Makky, et al. (2009). "New strategy for targeting of photosensitizers. Synthesis of glycodendrimeric phenylporphyrins, incorporation into a liposome membrane and interaction with a specific lectin." Chem Commun (Camb)(2): 224-226.

Barratt, G. (2003). "Colloidal drug carriers: achievements and perspectives." Cell Mol Life Sci 60(1): 21-37.

Barrett et al (Nat Genet. 2004 November; 36(11):1231-7),

Bazopoulou and Tavernarakis (Genetica. 2009 September; 137(1):39-46)

Beale E, Li G, Tan M W, Rumbaugh K P. *Caenorhabditis elegans* senses bacterial autoinducers. Appl Environ Microbiol. 2006 July; 72(7):5135-7.

Beutler E, Mitchell M: Special modifications of the fluorescent screening method for glucose-6-phosphate dehydrogenase deficiency. Blood 1968; 32:816-818

Boos, W. and H. Shuman (1998). "Maltose/maltodextrin system of *Escherichia coli*: transport, metabolism, and regulation." Microbiol Mol Biol Rev 62(1): 204-229.

Braungart, E., M. Gerlach, et al. (2004). "*Caenorhabditis elegans* MPP+ model of Parkinson's disease for high-throughput drug screenings." Neurodegener Dis 1(4-5): 175-183.

Brenner, S. (1974). "The genetics of *Caenorhabditis elegans*." Genetics 77(1): 71-94

Burns, A. R., I. M. Wallace, et al. (2010). "A predictive model for drug bioaccumulation and bioactivity in *Caenorhabditis elegans*." Nat Chem Biol 6(7): 549-557.

Burns A R, Kwok T C, Howard A, Houston E, Johanson K, Chan A, Cutler S R, McCourt P. Roy P J. High-throughput screening of small molecules for bioactivity and target identification in *Caenorhabditis elegans*. Nat Protoc. 2006; 1(4):1906-14.

Chhabra S R, Stea d P, Bainton N J, Salmond G P, Stewart G S, et al. (1993) Autoregulation of carbapenem biosynthesis in *Erwinia carotovora* by analogues of N-(3-oxo-hexa noyl)-L-hom oserine lactone. J Antibiot 46: 441-454.

Chhabra S R, Harty C, Hooi D S W, Daykin M, Williams P, et al. (2003) Synthetic Analogues of the Bacterial Signal (Quorum Sensing) Molecule N-(3-Oxododecanoyl)-L-homoserine Lactone as Immune Modulators. J Med Chem 46: 97-104.

Cole, R. D., G. L. Anderson, et al. (2004). "The nematode *Caenorhabditis elegans* as a model of organophosphate-induced mammalian neurotoxicity." Toxicol Appl Pharmacol 194(3): 248-256.

Dawlatsxina et al (2013, Nanoscale, 2013, 5, 11761); Microworms swallow the nanobait: the use of nanocoated microbial cells for the direct delivery of nanoparticles into *Caenorhabditis elegans*

De Araujo, C., D. Balestrino, et al. (2010). "Quorum sensing affects biofilm formation through lipopolysaccharide synthesis in *Klebsiella pneumoniae*." Res Microbiol 161(7): 595-603.

Dengg, M. and J. C. van Meel (2004). "*Caenorhabditis elegans* as model system for rapid toxicity assessment of pharmaceutical compounds." J Pharmacol Toxicol Methods 50(3): 209-214.

Fang-Yen, C., L. Avery, et al. (2009). "Two size-selective mechanisms specifically trap bacteria-sized food particles in *Caenorhabditis elegans*." Proc Natl Acad Sci USA 106(47): 20093-20096.

Ferenci, T. and K. S. Lee (1986). "Exclusion of high-molecular-weight maltosaccharides by lipopolysaccharide O-antigen of *Escherichia coli* and *Salmonella typhimurium*." J Bacteriol 167(3): 1081-1082.

Ferenci, T., M. Muir, et al. (1986). "Substrate specificity of the *Escherichia coli* maltodextrin transport system and its component proteins." Biochim Biophys Acta 860(1): 44-50.

Folkes L K, Christlieb M, Madej E, Stratford M R, Wardman P. Oxidative metabolism of combretastatin A-1 produces quinone intermediates with the potential to bind to nucleophiles and to enhance oxidative stress via free radicals. Chem Res Toxicol. 2007, (12):1885-94.

Frøkjaer-Jensen et al (Nat Genet. 2008 November; 40(11): 1375-83)

Fuqua, C. and E. P. Greenberg (2002). "Listening in on bacteria: acyl-homoserine lactone signalling." Nat Rev Mol Cell Biol 3(9): 685-695.

Gershon, H. and D. Gershon (2002). "*Caenorhabditis elegans*—a paradigm for aging research: advantages and limitations." Mech Ageing Dev 123(4): 261-274.

Hope M J, Bally M B, Webb G, Cullis P R. Production of large unilamellar vesicles by a rapid extrusion procedure: characterization of size distribution, trapped volume and ability to maintain a membrane potential. Biochim Biophys Acta. 1985; 812: 55-65.

Ishiguro, H., K. Yasuda, et al. (2001). "Enhancement of oxidative damage to cultured cells and *Caenorhabditis elegans* by mitochondrial electron transport inhibitors." IUBMB Life 51(4): 263-268.

Jansen et al. EMBO Journal, Vol. 21 No. 5 pp. 986-994, 2002

Jones A K, Buckingham S D, Sattelle D B. Chemistry-to-gene screens in *Caenorhabditis elegans*. Nat Rev Drug Discov. 2005, (4):321-30.

Klebba, P. E. (2002). "Mechanism of maltodextrin transport through LamB." Res Microbiol 153(7): 417-424.

Kramer K A, Oglesbee D, Hartman S J, Huey J, Anderson B, Magera M J, Matern D, Rinaldo P, Robinson B H, Cameron J M, Hahn S H. Automated spectrophotometric analysis of mitochondrial respiratory chain complex enzyme activities in cultured skin fibroblasts. Clin Chem. 2005 November; 51(11):2110-6.

Krien P M, Margou V, Kermici M: Electro-chemical determination of femtomole amounts of free reduced and oxidized gluta-thione. Application to human hair follicles. J Chromatogr 1992; 576:255-261

Kuwabara, P. E. and N. O'Neil (2001). "The use of functional genomics in *C. elegans* for studying human development and disease." J Inherit Metab Dis 24(2): 127-138.

Laing et al Biochem J. 2010 Dec. 15; 432(3):505-14

Lewis, J. A., Fleming, J. T. Basic culture methods. Methods in Cell Biology Vol. 48. *C. elegans*: Modern Biological Analysis of an Organism (eds. Epstein, H. F. & Shakes, D. C.) 3-29 (Academic Press, San Diego, Calif., 1995).

Lindblom, T. H. and A. K. Dodd (2006). "Xenobiotic detoxification in the nematode *Caenorhabditis elegans*." J Exp Zool A Comp Exp Biol 305(9): 720-730.

Makky, A., J. P. Michel, et al. (2011). "Biomimetic liposomes and planar supported bilayers for the assessment of glycodendrimeric porphyrins interaction with an immobilized lectin." Biochim Biophys Acta 1808(3): 656-666.

Mashburn-Warren, L., J. Howe, et al. (2008). "Interaction of quorum signals with outer membrane lipids: insights into prokaryotic membrane vesicle formation." Mol Microbiol 69(2): 491-502.

McCord J M, Fridovich I: Superoxide dismu-tase. An enzymic function for erythrocuprein (hemocuprein). J Biol Chem 1969; 244: 6049-6055

Murfitt, R. R., Vogel, K. & Sanadi, D. R. Characterization of the mitochondria of the free-living nematode, *Caenorhabditis elegans*. Comp. Biochem. Physiol., B 53, 423-430 (1976).

Noppl-Simson, D. A. and D. Needham (1996). "Avidin-biotin interactions at vesicle surfaces: adsorption and binding, cross-bridge formation, and lateral interactions." Biophys J 70(3): 1391-1401.

Paglia D E, Valentine W N: Studies on the quantitative and qualitative characterization of erythrocyte glutathione peroxidase. J Lab Clin Med 1967; 70:158-169

Putcha, G. V. and E. M. Johnson, Jr. (2004). "Men are but worms: neuronal cell death in *C. elegans* and vertebrates." Cell Death Differ 11(1): 38-48.

Qiu, Y., T. Zhang, et al. (1998). "Novel Nonionic Oligosaccharide Surfactant Polymers Derived from Poly(vinylamine) with Pendant Dextran and Hexanoyl Groups." Macromolecules 31(1): 165-171.

Riddle, D. L., T. Blumenthal, et al. (1997). "Introduction to *C. elegans*."

Robert and Bessereau (EMBO J. 2007 Jan. 10; 26(1):170-83),

Roh, J. Y., J. Lee, et al. (2006). "Assessment of stress-related gene expression in the heavy metal-exposed nematode *Caenorhabditis elegans*: a potential biomarker for metal-induced toxicity monitoring and environmental risk assessment." Environ Toxicol Chem 25(11): 2946-2956.

Santos, A. O., L. C. da Silva, et al. (2010). "Design of peptide-targeted liposomes containing nucleic acids." Biochim Biophys Acta 1798(3): 433-441.

Sengupta, P. and A. D. Samuel (2009). "*Caenorhabditis elegans*: a model system for systems neuroscience." Curr Opin Neurobiol 19(6): 637-643.

Shibamura, A., T. Ikeda, et al. (2009). "A method for oral administration of hydrophilic substances to *Caenorhabditis elegans*: Effects of oral supplementation with anti-oxidants on the nematode lifespan." Mech Ageing Dev 130(9): 652-655.

Shtonda, B. B. and L. Avery (2006). "Dietary choice behavior in *Caenorhabditis elegans*." J Exp Biol 209(Pt 1): 89-102.

Stiernagle, T., 1999. Maintenance of *C. elegans*. In: Hope, I. A. (Ed.), *C. elegans*: A Practical Approach. Oxford University Press, New York, pp. 51-67.

Stiernagle, T. Maintenance of *C. elegans* (Feb. 11, 2006), WormBook, ed. The *C. elegans* Research Community, WormBook Sudama et al, Metabolomics. 2013 February; 9(1):189-201)

Torchilin, V. P., T. S. Levchenko, et al. (2001). "p-Nitrophenylcarbonyl-PEG-PE-liposomes: fast and simple attachment of specific ligands, including monoclonal antibodies, to distal ends of PEG chains via p-nitrophenylcarbonyl groups." Biochim Biophys Acta 1511(2): 397-411.

Tsang, W. Y. and B. D. Lemire (2003). "The role of mitochondria in the life of the nematode, *Caenorhabditis elegans*." Biochim Biophys Acta 1638(2): 91-105.

Voorhies, W. A. V. (2002). "Metabolism and aging in the nematode *Caenorhabditis elegans*." Free Radical Biology and Medicine 33(5): 587-596.

Williams, P. L. et al. *Caenorhabditis elegans* as an alternative animal species. J. Toxicol. Environ. Health Part A 61, 641-647 (2000).

Wu et al, Chemosphere. 2012 June; 87(11):1281-7).

Xu, Z., J. Jayaseharan, et al. (2002). "Synthesis and characterization of oligomaltose-grafted lipids with application to liposomes." J Colloid Interface Sci 252(1): 57-65.

The invention claimed is:

1. A method for assessing the toxicity of a compound of interest comprising the steps of:
   (a) feeding a nematode with a nutrient composition comprising a carrier system, wherein the carrier system comprises a liposome containing said compound, wherein the liposome presents, on its surface, a tag substance that is chemo-attractive to said nematode, wherein the tag substance is selected from the group consisting of
   i) bacterial autoinducers, amino acids, nucleotides and vitamins; and
   ii) a whole bacterium linked to the carrier system by a linker substance,
      wherein ingestion of the compound in the carrier system by the nematode is increased as compared to ingestion of the compound without the carrier system; and
   (b) assessing whether the compound of interest reduces nematode survival, negatively impacts egg laying behavior or gonad functionality, increases embryonic lethality, or increases neuronal death,
   wherein a compound of interest which reduces nematode survival, which negatively impacts egg laying behavior or gonad functionality, increases embryonic lethality, or increases neuronal death, is a compound which is toxic, reprotoxic, teratogenic, or neurotoxic, respectively.

2. The method of claim 1, wherein the carrier system further comprises a fluorescent marker encapsulated in said liposome and wherein the fluorescence intensity of the co-absorbed fluorescent marker is measured thereby allowing quantification of the absorbed compound of interest.

3. The method of claim 1, wherein said tag substance is covalently linked to the surface of said liposome.

4. The method of claim 1, wherein said tag substance is selected from the group consisting of AI-2 and acylated homoserine lactones.

5. The method of claim 1, wherein said tag substance is biotin.

6. The method of claim 1, wherein said tag substance is a whole bacterium linked to the carrier system by a linker substance, and wherein said linker substance comprises maltose-based polysaccharides, wherein said maltose-based polysaccharides are polymers of covalently linked repeated units of maltose chosen from the group consisting of linear polymers, cyclic polymers, branched polymers and mixtures thereof.

7. The method of claim 6, wherein said linker substance is a maltodextrin or a maltodextrin analogue with a molecular weight up to 2000 g/mol.

8. The method of claim 5, wherein said tag substance is biotin and wherein said nutrient composition further comprises biotin and a biotin-binding protein which comprises at least two biotin-binding sites.

9. A method for promoting uptake of a compound of interest by a nematode comprising feeding a nematode with a carrier system, wherein the carrier system comprises a liposome containing said compound, wherein the liposome presents, on its surface, a tag substance that is chemo-attractive to said nematode, wherein the tag substance is selected from the group consisting of
   i) bacterial autoinducers, amino acids, nucleotides and vitamins; and
   ii) a whole bacterium linked to the carrier system by a linker substance,
   wherein ingestion of the compound in the carrier system by the nematode is increased as compared to ingestion of the compound without the carrier system.

10. The method of claim 9, wherein said tag substance is covalently linked to the surface of said liposome.

11. The method of claim 9, wherein said tag substance is selected from the group consisting of AI-2 and acylated homoserine lactones.

12. The method of claim 9, wherein said tag substance is biotin.

13. The method of claim 9, wherein said tag substance is a whole bacterium linked to the carrier system by a linker substance, and wherein said linker substance comprises maltose-based polysaccharides, wherein said maltose-based polysaccharides are polymers of covalently linked repeated units of maltose chosen from the group consisting of linear polymers, cyclic polymers, branched polymers and mixtures thereof.

14. The method of claim 13, wherein said linker substance is a maltodextrin or a maltodextrin analogue with a molecular weight up to 2000 g/mol.

15. The method of claim 12, wherein said tag substance is biotin and wherein said nutrient composition further comprises biotin and a biotin-binding protein which comprises at least two biotin-binding sites.

* * * * *